(12) United States Patent
Naseef

(10) Patent No.: US 11,637,644 B2
(45) Date of Patent: Apr. 25, 2023

(54) TEST SYSTEM AND METHOD FOR TESTING A MEDICAL DEVICE

(71) Applicant: Rohde & Schwarz GmbH & Co. KG, Munich (DE)

(72) Inventor: Mahmud Naseef, Planegg (DE)

(73) Assignee: ROHDE & SCHWARZ GMBH & CO. KG, Munich (DE)

( * ) Notice: Subject to any disclaimer, the term of this patent is extended or adjusted under 35 U.S.C. 154(b) by 0 days.

(21) Appl. No.: 17/392,464

(22) Filed: Aug. 3, 2021

(65) Prior Publication Data

US 2023/0038438 A1 Feb. 9, 2023

(51) Int. Cl.
*H04B 17/345* (2015.01)
*H04L 43/0823* (2022.01)
*H04L 67/12* (2022.01)
*A61N 1/372* (2006.01)

(52) U.S. Cl.
CPC ....... *H04B 17/345* (2015.01); *H04L 43/0823* (2013.01); *A61N 1/37252* (2013.01); *H04L 67/12* (2013.01)

(58) Field of Classification Search
CPC ... H04B 17/345; H04L 43/0823; H04L 67/12; A61N 1/37252
See application file for complete search history.

(56) References Cited

U.S. PATENT DOCUMENTS

| | | | |
|---|---|---|---|
| 9,621,201 B1 * | 4/2017 | Peric | H04B 1/0475 |
| 11,419,124 B2 * | 8/2022 | Yeh | H04J 11/005 |
| 2010/0110913 A1 * | 5/2010 | Min | H04B 17/345 |
| | | | 370/252 |
| 2020/0244564 A1 | 7/2020 | Naseef et al. | |
| 2022/0200777 A1 * | 6/2022 | Lee | H04L 5/14 |

OTHER PUBLICATIONS

"American National Standard for Evaluation of Wireless Coexistence", IEEE Standards Association, Accredited Standards Committee C63®—Electromagnetic Compatibility, dated Jan. 31, 2017, 77 pages.
"R&S@CMW Wideband Radio Communication Tester", Platform Overview, PD 5214.2833.12, Product Brochure, Version 05.00, dated Sep. 2019, 36 pages.

* cited by examiner

*Primary Examiner* — Chandrahas B Patel
(74) *Attorney, Agent, or Firm* — Westman, Champlin & Koehler, P.A.

(57) ABSTRACT

Improved testing of medical devices, in particular medical devices providing wireless communication capabilities. A communication link between a medical device under test and the communication tester is established and a signal quality indicator of the established communication link is monitored while interfering the communication link by one or more interfering signals.

21 Claims, 3 Drawing Sheets

TEST SYSTEM AND METHOD FOR TESTING A MEDICAL DEVICE

TECHNICAL FIELD

The present invention relates to a test system for testing a medical device. The present invention further relates to a method for testing a medical device. In particular, the present invention relates to testing of a medical device including a wireless communication interface.

BACKGROUND

Even though applicable in general to any kind of medical device providing wireless communication capabilities, the present invention and its underlying problem will be hereinafter described in connection with implanted or body worn medical devices such as cardiac pacemaker or the like.

Many modern medical devices such as cardiac pacemakers or the like provide wireless communication capabilities. In this way, a wireless communication link may be established with a remote device. The remote device may be used for adjusting settings of the medical device or reading out device data of the medical device. Especially in the context of medical devices, a particularly high level of security with respect to electromagnetic compatibility (EMC) must be ensured.

The American national standard for evaluation of wireless coexistence ANSI C63.27 describes an evaluation process and test methods to qualify the ability of wireless devices to coexist with other wireless services in a radio frequency environment.

Conventional test methods usually only apply a high-power EMC test signal, in order to evaluate a functionality of the device under test.

SUMMARY

Against this background, there is a need for an improved testing of medical devices, in particular medical devices providing wireless communication capabilities. In particular, there is a need for an improved evaluation of a wireless transmission performance provided by a medical device in an environment of electromagnetic interferences.

The present invention provides a test system and method for testing a medical device, in particular a medical device providing wireless communication capabilities, with the features of the independent claims. Further advantageous embodiments are subject matter of the dependent claims.

According to a first aspect, a test system for testing a medical device is provided. The test system comprises a communication tester and a first interference signal generator. The communication tester is configured to establish a wireless communication link with the medical device. The communication tester is further configured to determine a signal quality indicator of the established wireless communication link. The first interference signal generator is configured to emit a first wireless interfering signal. The first wireless interfering signal is used for interfering the wireless communication link established between the communication tester and the medical device. Accordingly, the communication tester may determine the signal quality indicator of the wireless communication link while the first interference signal generator emits the first wireless interfering signal.

According to a further aspect, a method for testing a medical device is provided. The method comprises establishing a wireless communication link with the medical device. The wireless communication link may be established by a communication tester. The method further comprises emitting a first wireless interfering signal. The first wireless interfering signal may be used for interfering the wireless communication link. The first wireless interfering signal may be emitted by a first interference signal generator. The method further comprises determining a signal quality indicator of the wireless communication link. The signal quality indicator may be determined by the communication tester.

Many modern medical devices provide capabilities for wireless communication. Especially, a wireless communication link may be established with a remote device for receiving settings of the medical device and/or reading out device data of the medical device. Especially in the field of medical devices, it is very important that a reliable communication between the medical device and the remote device can be performed. For this purpose, it is not only necessary that the operation of the medical device is not disturbed by electromagnetic interferences, but also a reliable and undisturbed data exchange between the medical devices and remote device via a wireless communication link can be performed.

Based on this finding, the present invention provides an improved approach for testing a medical device, in particular a medical device providing wireless communication capabilities. For this purpose, a communication tester establishes a wireless communication link with the medical device and evaluates the transmission properties via this wireless communication link while one or more wireless interfering signals are applied to the test scenario. Based on the analysis of the wireless communication link applied with impact of the one or more wireless interfering signals, a signal quality indicator such as a packet error rate or the like is determined. Accordingly, a robustness of the wireless communication in view of the wireless interfering signals can be analyzed.

In this way, the robustness of a communication link established between a medical device and a remote device can be tested and evaluated. Especially, any kind of medical device can be tested. For example, medical devices such as implanted or body worn medical devices, e.g., cardiac pacemakers or the like can be tested. However, the testing of medical devices may be also applied to patient monitoring devices or systems which provide wireless communication capabilities. However, it is understood, that the testing of the medical devices, in particular of the robustness of the wireless communication link of medical devices may be also applied to any other kind of medical device.

The communication tester which is used for establishing the wireless communication link and determining the signal quality indicator may be any kind of appropriate communication test device. For example, a wideband radio communication tester such as Rohde & Schwarz® CMW Wideband Radio Communication Testers may be used especially, a R&S® CMW 500 may be used as communication tester for establishing a wireless communication link with the medical device and determining an appropriate signal quality indicator. However, it is understood, that any other kind of appropriate device for establishing a wireless communication link based on a desired communication standard may be used, too.

The communication between the medical device and the communication tester may relate to any kind of appropriate communication standard or a proprietary communication scheme. For example, communication based on WIFI, Bluetooth or any other communication standard may be used.

The first interference signal generator as well as any further interference signal generators which will be further mentioned below, may be any kind of appropriate signal generator which provides a desired wireless interfering signal. The interference signal generator may generate an interfering signal having a specific frequency or relating to a specific frequency band or channel. For example, the generated interfering signal may relate to a specific WIFI channel. Further, the interference signal generator is configured to adjust a signal strength or an interfering power of the emitted wireless interfering signal. For this purpose, the interference signal generator may comprise any kind of appropriate element such as radio frequency signal sources, modulators, mixers, amplifiers, attenuators or the like. Furthermore, the interference signal generator may comprise a controller for controlling the operation of the signal generation. The interference signal generator may further comprise a communication interface for communicatively coupling the interference signal generator with further devices in order to receive commands or settings which may be used for controlling the operation of the interference signal generator.

Based on this approach, namely the analysis of a signal quality indicator of a wireless communication link between the medical device and the communication tester while the wireless communication link is interfered by at least one wireless interfering signal, it is possible to test the robustness of the wireless communication. In this way, critical configurations can be identified. Further, it is possible to determine and evaluate safety margins in order to ensure a reliable and robust wireless communication between the medical device and a remote communication partner. Furthermore, the obtained data of such a test for a medical device may be used in order to further improve the configuration or design of the medical device.

Further embodiments of the present invention are subject of the further subclaims and of the following description, referring to the drawings.

In a possible embodiment, the signal quality indicator which is determined by the communication tester comprises at least a packet error rate. Such a packet error rate may specify a ratio between packets which are considered to be erroneous and all packets which are transmitted and/or received data packets via the established communication channel. For example, erroneous packets may be identified by using a checksum of a data packet or any other appropriate measure for verifying a data packet. In case that an error correction approach may be applied, an erroneous packet may be considered as a packet which cannot be correctly recovered by the error correction approach.

In a possible embodiment, the test system further comprises a second interference signal generator. The second interference signal generator may be configured to emit a second wireless interfering signal. The second wireless interfering signal may be used for interfering with the wireless communication link established between the communication tester and the medical device. The second interference signal generator may be realized in a same or similar manner as the first interference signal generator. In this way, the robustness of the established wireless communication channel based on two interference signals can be tested.

In a possible embodiment, the test system comprises a third interference signal generator. The third interference signal generator is configured to emit a third wireless interfering signal for interfering with the wireless communication link established between the communication tester and the medical device. The third interference signal generator may be also realized in a same or similar manner as the first and/or second interference signal generator. Accordingly, the established wireless communication channel may be tested under the impact of three wireless interfering signals.

In a possible embodiment, the test system comprises at least one further interference signal generator. Each of the further interference signal generators may be also realized in a same or similar manner as the previously described first, second and/or third interference signal generators. Accordingly, the test system may comprise four or more interference signal generators for generating wireless interfering signals for interfering with the wireless communication link established between the communication tester and the medical device. In this way, the arrangement of the test system may comprise four, five up to even fifty or more interference signal generators each emitting a wireless interfering signal.

In a possible embodiment, the first wireless interfering signal, the second wireless interfering signal, the third wireless interfering signal and each of the further wireless interfering signals relate to a same frequency or channel. In particular, the frequency, frequency band or channel used for generating the wireless interfering signals may be the same or relate to the frequency, frequency band or channel used for establishing the communication link between the medical device and the communication tester. In this way, the impact of multiple interfering sources on the communication link can be evaluated.

In a possible embodiment, the second wireless interfering signal, the third wireless interfering signal and each of the further wireless interfering signals have a same interference power or signal strength. In such a configuration, the interference power or signal strength of the first wireless interfering signal may be changed, while maintaining the remaining wireless interfering signals having a constant, especially same interference power or signal strength. Accordingly, the robustness of the communication channel can be evaluated in such a configuration. Since the robustness of the communication channel with regard to a first wireless interfering signal may be more critical if there are further wireless interfering signals in the background, evaluation of such scenarios may provide important information for assessing the reliability of the established communication channel with regard to interfering signals.

In a possible embodiment, the test system comprises a test controller. The test controller may control the operation of the individual devices and components which are involved in the testing of the medical device. In particular, the test controller is configured to determine a first interference power level corresponding to the interference power emitted by the first interference signal generator at which a predetermined packet error rate is reached. For this purpose, the test controller may continuously or stepwise increase the interference power emitted by the first interference signal generator until the predetermined packet error rate is reached. Again, the wireless interfering signal of the first interference signal generator can be evaluated even in a scenario when there are emitted multiple further wireless interfering signals by the second interference signal generator, the third interference signal generator and, if used, further interference signal generators.

If the predetermined packet error rate is not reached, i.e., the packet error rate always remains below the predetermined packet error rate, until a maximum interference power is reached, the above-described procedure by increasing the interference power may be stopped, and a spatial distance between the medical device and interference signal generators, in particular the antenna of the interference signal generators may be reduced. After this, the test procedure may be repeated.

In a possible embodiment, the test controller is configured to determine a first interference power level which corresponds to the interference power emitted by the first interference signal generator at which the predetermined packed error rate is reached while the second interference signal generator and, if used, the third and further signal generators emit interference signals having an initial interference signal power. Further, the test controller may determine a second interference power level which corresponds to interference power emitted by the first interference signal generator at which the predetermined packed error rate is reached while the other interference signal generators, i.e., the second interference signal generator, the third interference signal generator and further interference signal generators do not emit interference signals. In this way, the robustness of the wireless communication channel can be evaluated by comparing the determined first interference power level and determined second interference power level. Based on this, an impact of the additional wireless interfering signals from the second, third and further interference signal generators can be evaluated.

In a possible embodiment, the test controller is configured to control a frequency, frequency band or channel of the communication link. Additionally or alternatively, the test controller may be also configured to control a frequency, frequency band or channel of the first, second, third and/or further interference signals. Accordingly, the test system, in particular the test controller may determine individual first and second interference power levels for a number of at least two different frequencies, frequency bands or channels. In particular, multiple individual first and second interference power levels may be determined for all frequencies, frequency bands or channels which may be used by the medical device for establishing wireless communication links.

In a possible embodiment, the test system comprises a mechanical positioning device. The mechanical positioning device may be configured to control and change an orientation of the medical device. In particular, the orientation of the medical device may be changed with respect to a direction of the communication link established between the medical device and the communication tester. The mechanical positioning device may comprise a controlled motor or any other active actuator for an automated control of the position and/or orientation of the medical device.

With the present invention it is therefore possible to test the robustness of a wireless communication link established between a medical device under test and a further communication partner. In particular, it is possible to evaluate the impact of wireless interference signals on a wireless communication between the medical device under test and a further communication partner. For this purpose, a signal quality indicator of the established communication link between the medical device under test and the communication partner is measured and evaluated while a number of one or more wireless interfering signals are applied to the test scenario with the medical device under test and the communication partner. Such a signal quality indicator may be, for example a packet error rate. Especially, the robustness of the established wireless communication link may be evaluated even when applying multiple wireless interfering signals simultaneously. Such testing of a medical device provides valuable information for assessing the reliability and robustness of the medical device and for further improving the design of medical devices.

BRIEF DESCRIPTION OF THE DRAWINGS

For a more complete understanding of the present invention and advantages thereof, reference is now made to the following description taking in conjunction with the accompanying drawings. The invention is explained in more detail below using exemplary embodiments, which are specified in the schematic figures and the drawings, in which.

DESCRIPTION OF EMBODIMENTS

Figure 1:
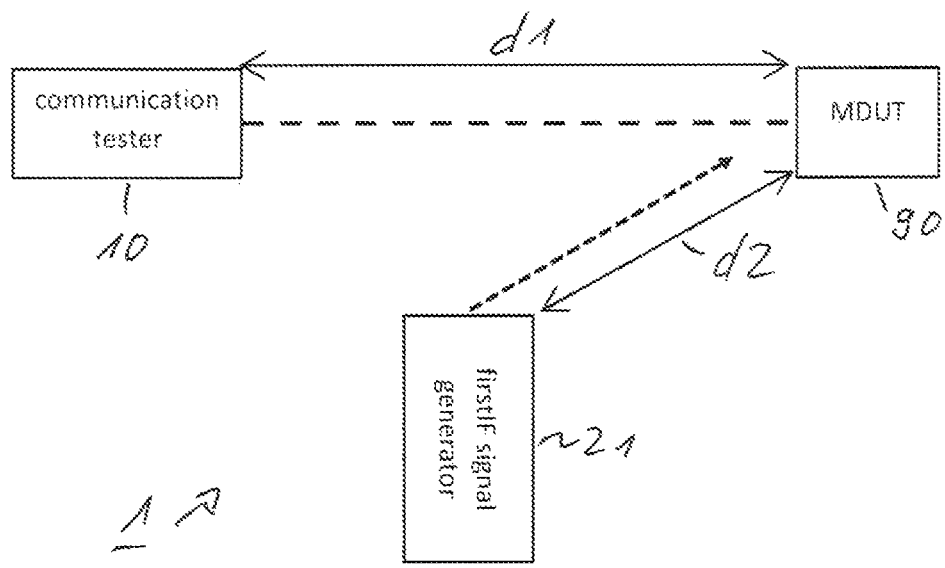
FIG. 1: shows a schematic block diagram of a test system according to an embodiment.

FIG. 1 shows a schematic block diagram of a test system 1 for testing a medical device under test (MDUT) 90 according to an embodiment. The medical device under test 90 may be any kind of medical device. For example, the MDUT 90 may be a cardiac pacemaker or any other implanted medical device or body worn medical device. However, any other medical device, in particular medical devices which can establish a wireless communication via wireless communication link may be possible, too. In order to establish such a wireless communication link, the medical device may comprise a wireless communication interface. The wireless communication link may be established, for example by means of a standard communication protocol or a proprietary communication protocol. For example, the communication link may be established via a wireless communication in a WIFI band. However, any other kind of communication for establishing a wireless communication link may be possible, too.

The test system 1 comprises a communication tester 10 and at least a first interference signal generator 21. Communication tester 10 may establish a wireless communication link with the MDUT 90. For this purpose, communication tester 10 may comprise all required components for emitting and receiving wireless signals, in particular radio frequency signals such as an antenna, RF signal generators, mixers, modulators, demodulators, amplifiers, attenuators, filters etc. Further, communication tester 10 may comprise a processing device for processing data which are transmitted to the MDUT 90 or received from the MDUT 90 via the established wireless communication link. In particular, the data transmission between the communication tester 10 and the MDUT 90 may be performed based on a packet-based data transmission. Accordingly, communication tester 10 may transmit data packets to the MDUT 90 via the established communication link and/or receive data packets from the MDUT 90.

In order to evaluate the quality of the established transmission link between the communication tester 10 and the MDUT 90, at least one signal quality indicator may be determined. For example, communication tester 10 may analyze the received data packets in order to determine a packet error rate (PER). Such a PER may specify a ratio between received packets which are considered to be erroneous and a sum of all received packets. For example, a PER may be determined for a particular number of received packets or for packets received within a predetermined period of time. However, it may be also possible to use any other appropriate measure for characterizing an appropriate signal quality indicator.

Communication tester 10, in particular the antenna of communication tester 10 which is used for establishing the wireless communication link with MDUT 90 may be arranged at a predetermined distance d1 from MDUT 90.

In order to test the robustness of the MDUT 90, in particular the data transfer by the established communication link between the MDUT 90 and the communication tester 10, a number of one or more wireless interference signals may be applied to the test scenario. For this purpose, a first interference signal generator 21 is provided in the test system 1. First interference signal generator 21 may generate and emit interference signals. For this purpose, first interference signal generator 21 may comprise any kind of appropriate components such as RF signal generators, mixers, modulators, amplifiers, attenuators, filters etc. Further, first signal generator 21 may comprise an emitting antenna for emitting the generated interference signal. In particular, the generated interference signals may be emitted in the direction to MDUT 90. For example, the antenna for emitting the interference signal may be located at a predetermined distance d2 from the MDUT 90. Further, the antenna for emitting the interference signal may be located at a predetermined position with respect to an orientation of MDUT 90.

First interference signal generator 21 may generate and emit a first wireless interference signal. Especially, this first wireless interference signal may have predetermined characteristics, for example a predetermined interference power or signal strength, a predetermined frequency or frequency band or channel, predetermined modulation or other particular characteristics.

Communication tester 10 may determine one or more signal quality indicators while first interference signal generator 21 emits the first interfering signal. In this way, an impact of the emitted interfering signal on the established communication link can be determined. For example, a change of the signal quality indicator, for example the packet error rate, depending on the characteristics of the emitted interfering signal can be determined. In a possible example, the signal strength or interfering power of the emitted interfering signal may be continuously or stepwise increased, and at the same time the signal quality indicator may be monitored. In this way, it is possible to determine a power level of the interfering signal when the signal quality indicator falls below a predetermined threshold value, for example when the packet error rate exceeds above a predetermined threshold.

Figure 2:
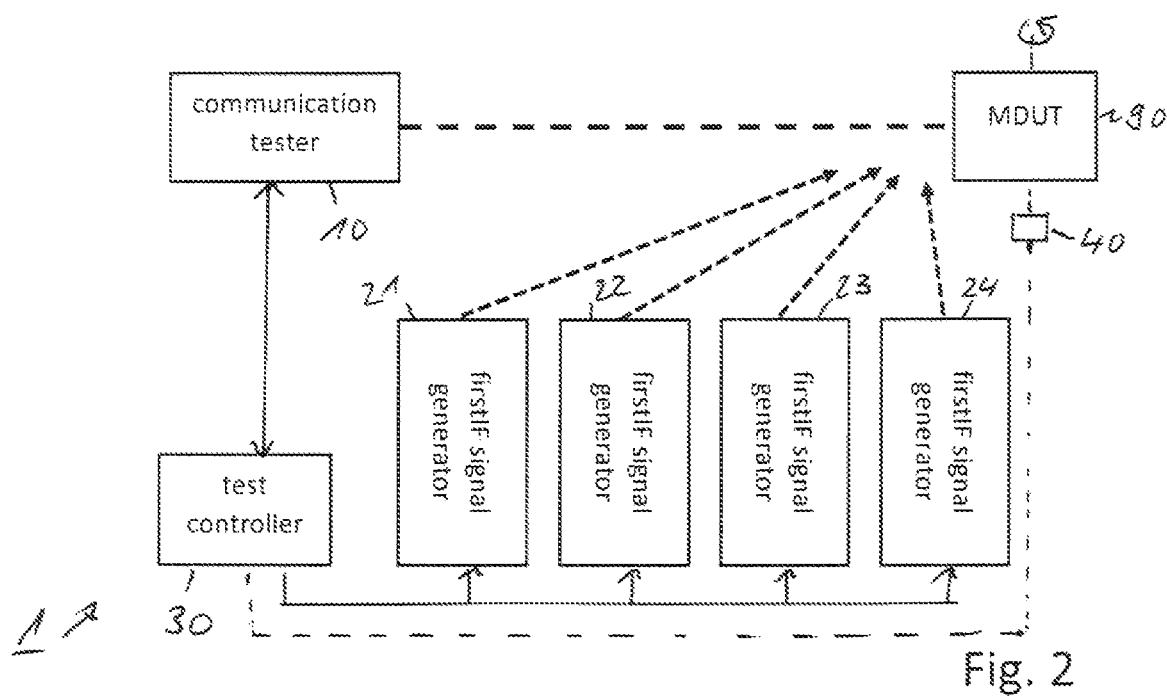
FIG. 2: shows a schematic block diagram of a test system according to further embodiment.

FIG. 2 shows a test system 1 according to a further embodiment. The test system 1 according to FIG. 2 mainly corresponds to the previously described embodiment according to FIG. 1. Thus, all explanations provided in connection with FIG. 1 also apply to the embodiment of FIG. 2.

As can be seen in FIG. 2, test system 1 may comprise not only one first interference signal generator 21 but also a second test signal generator 22, a third test signal generator 23 or even one or more further test signal generators 24. In other words, any number of test signal generators 21-24 may be possible. For example, test system 1 may comprise a number of up to 50 test signal generators.

Each test signal generator 21-24 may individually generate an interfering signal and emit the generated interfering signal. However, it may be also possible to use one or more common interference signal generators which generate multiple interfering signals. In this way, each of the multiple generated interfering signal may be emitted by a separate antenna. However, it may be also possible to emit multiple interfering signals by means of a common antenna.

The generation and the properties of each wireless interference signal which is generated and emitted by anyone of the first, second, third or further interference generators 21-24 may correspond to the explanation as already provided above in connection with the first interference signal generator 21.

Accordingly, multiple wireless interfering signals may be applied in test system 1 by means of the multiple interference generators 21-24.

In a possible example, all interference signal generators 21-24 may generate and emit interfering signals having a same frequency or relating to a same frequency range or channel. For example, the frequency, frequency range or channel of the interference signals may correspond to the frequency, frequency band or channel used for establishing the wireless communication channel between the communication tester 10 and the MDUT 90. However, it may be also possible that the properties of the interfering signals generated by the interference signal generators 21-24 may be configured individually for each interference signal generator 21-24.

In a possible example, the operation of the interference signal generators 21-24 may be controlled by a test controller 30. For this purpose, test controller 30 may be communicatively coupled with the interference signal generators 21-24. Accordingly, test controller 30 may individually set frequency, frequency range or channel of each interference signal generator 21-24. Further, the interference power or signal strength of the emitted interference signals may be also controlled by test controller 30. However, it is understood, that any other property of the generated and emitted interference signals may be also controlled and configured by test controller 30.

Test system 1 may further comprise a mechanical positioning device 40. Mechanical positioning device 40 may adjust the orientation or spatial position of MDUT 90. In particular, the position or orientation of MDUT 90 may be adjusted with respect to the position of communication tester 10, in particular the antenna of communication tester 10 used for establishing the wireless communication link. It may be also possible to adjust the orientation or position of MDUT 90 with respect to the interference signal generators 21-24, in particular the one or more antennas used for emitting the wireless interference signals. For this purpose, mechanical positioning device 40 may comprise a motor or any other kind of actor for moving or rotating the MDUT 90. In particular, the positioning performed by mechanical positioning device 40 may be controlled by test controller 30.

Figure 3:
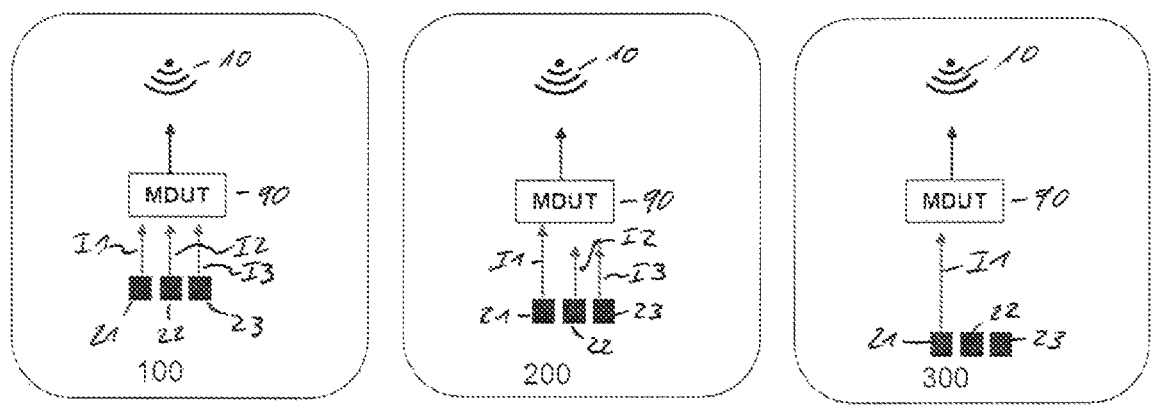
FIG. 3: shows a schematic diagram illustrating a test schema according to an embodiment.

In the following, an exemplary test scheme for testing a medical device under test 90 will be described in connection with FIG. 3. In this example, three interference signal generators 21, 22 and 23 are used. However, it is understood, that any other appropriate number of interference signal generators 21-24 may be possible, too.

In a first operation mode 100, a wireless communication link is established between communication tester 10 and MDUT 90. Further, the first, second and third interference signal generators 21-23 are operated such that each interference signal generator 21-23 emits a wireless interference signal I1, I2, I3 having a same initial interference power.

Accordingly, communication tester 10 may determine an initial signal quality indicator, for example an initial packet error rate.

In this first operation mode, all interference signal generators 21-23 may generate interference signals having not only a same interference power, but also same properties such as frequency, frequency range or channel.

In a second operation mode 200, the interference power or signal strength of the first interfering signal I1 emitted by the first interference signal generator 21 is increased over time, while the properties of the further, i.e., the second and third interfering signal I2, I3 are maintained to be the same as in the first operation mode 100.

The increase of the interference power of the first interfering signal I1 may be performed continuously or stepwise. At the same time, the signal quality indicator, for example the packet error rate may be monitored by the communication tester 10. This process of increasing the interference power of the first interfering signal I1 is performed until the signal quality indicator of the communication link between the MDUT 90 and the communication tester 10 falls below a predetermined threshold value. For example, the interference power provided by the first interfering signal I1 may be increased until the packet error rate PER exceeds above a predetermined threshold, for example 10%. In this way, an interference power level is determined which leads to the effect that the signal quality indicator falls below the predetermined threshold value, especially the PER raises above a predetermined value, e.g., 10%.

In a further, third operation mode 300, the second and third interference signal generators 22 and 23 do not emit interfering signals. Thus, only first interference signal generator 21 generates a first interfering signal I1. Again, the interference power of the first interfering signal I1 is continuously or stepwise increased until the signal quality indicator of the communication link between the MDUT 90 and the communication tester 10 falls below a predetermined threshold value, for example, the packet error rate PER exceeds above a predetermined threshold, e.g., 10%.

If the interference power of the first interfering signal I1 is increased up to a maximum interference power level in the second or third operation mode 200, 300, the operation may be stopped, and the distance between the MDUT 90 and the signal interference generators 21-23, in particular the antennas emitting the interfering signals may be reduced. After this, the above-described operation based on operational modes 100, 200 and 300 may be repeated.

After completing operation modes 100, 200 and 300 and determining the respective interference power levels, the procedure may be repeated for different orientations of the MDUT 90 and/or different frequencies, frequency bands or channels.

Figure 4:
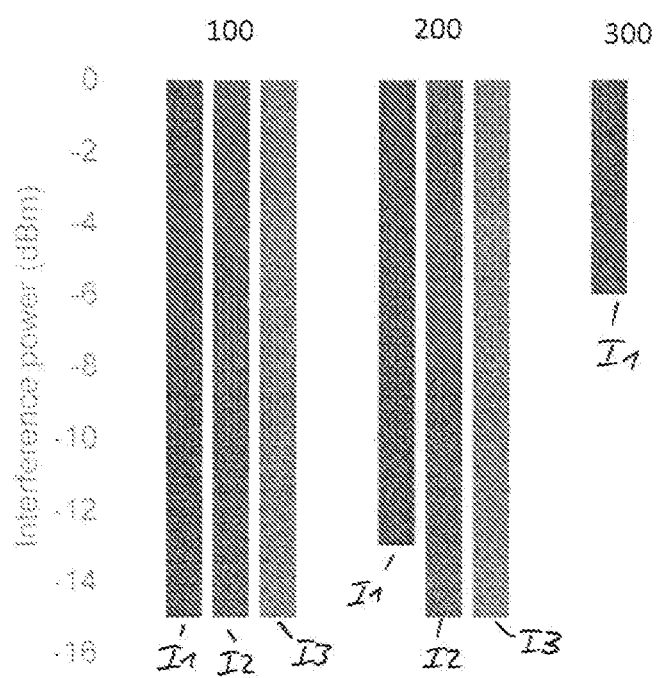
FIG. 4: shows a schematic diagram illustrating power levels of interfering signal during a test scenario according of an embodiment.

FIG. 4 shows an exemplary measurement result of a test procedure according to the test scenario described in connection with FIG. 3. In the left part of FIG. 4, all three interference signal generators 21, 22, 23 emit interfering signals with an initial interference power of −15 dBm.

As can be seen in the middle of FIG. 4, the interference power of the first interfering signal I1 is increased up to −13 dBm. At this interference power level, the signal quality indicator, especially the packet error rate has reached a threshold value of 10%. The second and third interfering signal I2 and I3 are maintained at the initial interference power level of −15 dBm.

In the right part of FIG. 4, the second and third interference signal generator do not emit any interference signal. Accordingly, the threshold value of the signal quality indicator of a packet error rate of 10% is reached by an interference power level of −6 dBm of the first interference signal I1.

Hence, it can be recognized that if there exist additional interference sources such as the second and third wireless interference signal I2 and I3, a critical signal quality indicator such as a required packet error rate may be reached earlier even by a first interference signal I1 having a lower interference power. Such a case may be a more critical operational mode of the medical device under test 90 than only considering a single interference signal.

Figure 5:
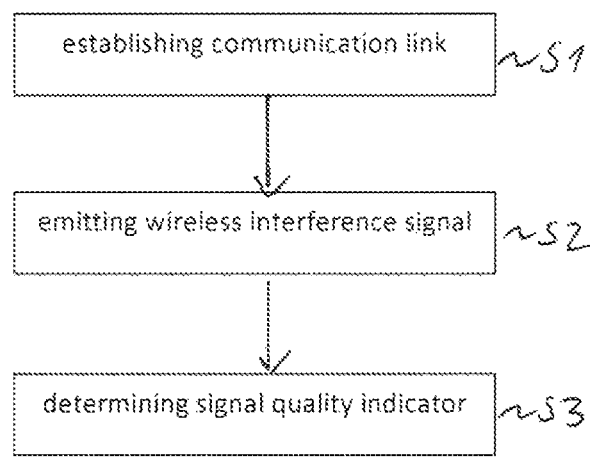
FIG. 5: shows a flow diagram illustrating a test method according to an embodiment.

FIG. 5 shows a flow diagram illustrating a method for testing a medical device MDUT 90 according to an embodiment. The method may comprise any appropriate steps as already described above in connection with the test system 1. Test system 1 as described above may comprise any appropriate device configured to perform an operation as described below in connection with the method for testing the medical device 90.

In step S1, a wireless communication link may be established between a communication tester 10 and the medical device 90.

In step S2, a first wireless interfering signal is emitted for interfering the wireless communication link established between the communication tester 10 and the medical device 90. The first wireless interfering signal may be generated by a first interference signal generator 21.

In step S3, the signal quality indicator of the wireless communication link may be determined. The determination may be performed by the communication tester 10.

Especially, the signal quality indicator may comprise a packet error rate PER.

The method may further comprise a step of emitting a second wireless interfering signal for interfering the wireless communication link established between the communication tester 10 and the medical device 90. The second wireless interfering signal may be emitted by a second interference signal generator 22.

Further, the method may comprise a step of emitting a third wireless interfering signal for interfering the wireless communication link established between the communication tester 10 and the medical device 90. The third wireless interfering signal may be emitted by a third interference signal generator 23.

The method may comprise further emitting further wireless interfering signals, wherein each further wireless interfering signal is emitted by a further interference signal generator.

The first wireless interfering signal, the second wireless interfering signal, the third wireless interfering signal and/or each of the further wireless interfering signal may relate to a same frequency, frequency band or channel.

The second wireless interfering signal, the third wireless interfering signal and/or each of the further wireless interfering signal may have a same interference power while testing the medical device under test 90.

The method may further comprise controlling an interference power emitted by the first interference signal generator 21 and increasing the interference power emitted by the first interference signal generator until a predetermined packet error rate, for example 10% is reached. The method may further comprise determining a first interference power level which corresponds to the interference power of the first wireless interfering signal at which the predetermined packet error rate is reached while the second wireless interfering signal and the third wireless interfering signal have an initial interference signal power level. Further, the method may comprise determining a second interference power level which corresponds to the interference power of the first wireless interfering signal at which the predetermined packet error rate is reached while no other, in particular no second, no third and no further wireless interfering signal is emitted.

The method may further comprise controlling frequency, frequency band or channel of the communication link and/or the first, second and/or further interference signals. Further, individual first and second interference power levels may be determined for a number of at least two different frequencies, frequency bands or channels.

The method may further comprise changing an orientation or position of the medical device under test 90 with respect to a direct of the communication link, the communication tester 10 or the position of the interference signal generators. The position and/or orientation may be changed by a mechanical positioning device.

Summarizing, the present invention relates to an improved testing of medical devices, in particular medical devices providing wireless communication capabilities. A communication link between a medical device under test and the communication tester is established and a signal quality indicator of the established communication link is monitored while interfering the communication link by one or more interfering signals.

In the foregoing detailed description, various features are grouped together in one or more examples or examples for the purpose of streamlining the disclosure. It is understood that the above description is intended to be illustrative, and not restrictive. It is intended to cover all alternatives, modifications and equivalents as may be included within the scope of the invention. Many other examples will be apparent to one skilled in the art upon reviewing the above specification.

Specific nomenclature used in the foregoing specification is used to provide a thorough understanding of the invention. However, it will be apparent to one skilled in the art in light of the specification provided herein that the specific details are not required in order to practice the invention. Thus, the foregoing descriptions of specific embodiments of the present invention are presented for purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. Throughout the specification, the terms "including" and "in which" are used as the plain-English equivalents of the respective terms "comprising" and "wherein," respectively. Moreover, the terms "first," "second," and "third," etc., are used merely as labels, and are not intended to impose numerical requirements on or to establish a certain ranking of importance of their objects.

LIST OF REFERENCE SIGNS

1 test system
10 communication tester
21 first interference signal generator
22 second interference signal generator
23 third interference signal generator
24 further interference signal generator
30 test controller
40 mechanical positioning device
90 medical device under test
100 first operation mode
200 second operation mode
300 third operation mode
I1, I2, I3 interference signal levels
S1, S2, S3 method steps

The invention claimed is:

1. A test system for testing a medical device, the test system comprising:
 a communication tester configured to establish a wireless communication link with the medical device and determine a signal quality indicator of the wireless communication link;
 a first interference signal generator configured to emit a first wireless interfering signal for interfering with the wireless communication link established between the communication tester and the medical devices; and
 a mechanical positioning device configured to change an orientation of the medical device with respect to a direction of the communication link.

2. The test system of claim 1, wherein the signal quality indicator determined by the communication tester comprises a packet error rate.

3. The test system of claim 1, comprising a second interference signal generator configured to emit a second wireless interfering signal for interfering with the wireless communication link established between the communication tester and the medical device.

4. The test system of claim 3, comprising a third interference signal generator configured to emit a third wireless interfering signal for interfering with the wireless communication link established between the communication tester and the medical device.

5. The test system of claim 4, comprising at least one further interference signal generator, wherein each of the at least one further interference signal generator is configured to emit a further wireless interfering signal for interfering with the wireless communication link established between the communication tester and the medical device.

6. The test system of claim 5, wherein the first wireless interfering signal, the second wireless interfering signal, the third wireless interfering signal and each of the further wireless interfering signals relates to a same frequency or channel.

7. The test system of claim 5, wherein the second wireless interfering signal, the third wireless interfering signal and each of the further wireless interfering signals have a same interference power.

8. The test system of claim 5, wherein the test controller is configured to control a frequency or channel of the communication link and/or the first, second, third and/or further interference signals, and
 the test controller is configured to determine individual first interference power levels and second first interference power levels for a number of at least two different frequencies or channels.

9. The test system of claim 4, comprising a test controller configured to control an interference power emitted by the first interference signal generator and to increase the interference power emitted by the first interference signal generator until a predetermined packet error rate is reached.

10. The test system of claim 9, wherein the test controller is configured to determine a first interference power level which corresponds to the interference power emitted by the first interference signal generator at which the predetermined packed error rate is reached while the second interference signal generator and the third signal generator emit interference signals having a constant initial interference signal power, and the test controller is configured to determine a second interference power level which corresponds to the interference power emitted by the first interference signal generator at which the predetermined packed error rate is reached while the second interference signal generator and the third interference signal generator do not emit interference signals.

11. A test system for testing a medical device, the test system comprising:
a communication tester configured to establish a wireless communication link with the medical device and determine a signal quality indicator of the wireless communication link;
a first interference signal generator configured to emit a first wireless interfering signal for interfering with the wireless communication link established between the communication tester and the medical device;
a second interference signal generator configured to emit a second wireless interfering signal for interfering with the wireless communication link established between the communication tester and the medical device;
a third interference signal generator configured to emit a third wireless interfering signal for interfering with the wireless communication link established between the communication tester and the medical device;
at least one further interference signal generator, wherein each of the at least one further interference signal generator is configured to emit a further wireless interfering signal for interfering with the wireless communication link established between the communication tester and the medical device; and
wherein the second wireless interfering signal, the third wireless interfering signal and each of the further wireless interfering signals have a same interference power.

12. A method for testing a medical device, the method comprising:
establishing, by a communication tester, a wireless communication link with the medical device;
emitting, by a first interference signal generator, a first wireless interfering signal for interfering with the wireless communication link established between the communication tester and the medical device; and
determining, by the communication tester, a signal quality indicator of the wireless communication link; and
changing, by a mechanical positioning device, an orientation of the medical device with respect to a direction of the communication link.

13. The test method of claim 12, wherein the determined signal quality indicator comprises a packet error rate.

14. The test method of claim 12, further comprising emitting, by a second interference signal generator, a second wireless interfering signal for interfering with the wireless communication link established between the communication tester and the medical device.

15. The test method of claim 14, further comprising emitting, by a third interference signal generator, a third wireless interfering signal for interfering with the wireless communication link established between the communication tester and the medical device.

16. The test method of claim 15, further comprising emitting, by each of at least one further interference signal generator, a further wireless interfering signal, respectively, for interfering with the wireless communication link established between the communication tester and the medical device.

17. The test method of claim 16, wherein the first wireless interfering signal, the second wireless interfering signal, the third wireless interfering signal and each of the further wireless interfering signals relates to a same frequency or channel.

18. The test method of claim 16, wherein the second wireless interfering signal, the third wireless interfering signal and each of the further wireless interfering signals have a same interference power.

19. The test method of claim 16, further comprising controlling an interference power emitted by the first interference signal generator and increasing the interference power emitted by the first interference signal generator until the packet error rate is reached.

20. The test method of claim 19, further comprising
determining a first interference power level which corresponds to the interference power of the first wireless interfering signal at which the predetermined packed error rate is reached while the second wireless interfering signal and the third wireless interfering signal ere emitted with constant initial interference signal power, and
determining a second interference power level which corresponds to the interference power of the first wireless interfering signal at which the predetermined packed error rate is reached while no second wireless interfering signal and no third wireless interfering signal is emitted.

21. The test method of claim 16, further comprising
controlling a frequency or channel of the communication link and/or the first, second, third and/or further interference signals, and
determining individual first interference power levels and second first interference power levels for a number of at least two different frequencies or channels.

* * * * *